United States Patent
Grimard (10) Patent No.: US 8,196,807 B2
(45) Date of Patent: Jun. 12, 2012

(54) METHOD OF IDENTIFYING A CONTAINER AND/OR A FINISHED ARTICLE OBTAINED FROM THE SAID CONTAINER, IN PARTICULAR FOR MEDICAL USE

(75) Inventor: Jean-Pierre Grimard, Vif (FR)

(73) Assignee: Becton Dickinson France S.A.S. (FR)

( * ) Notice: Subject to any disclaimer, the term of this patent is extended or adjusted under 35 U.S.C. 154(b) by 162 days.

(21) Appl. No.: 11/912,910

(22) PCT Filed: Apr. 26, 2006

(86) PCT No.: PCT/IB2006/001734
§ 371 (c)(1),
(2), (4) Date: Jun. 16, 2008

(87) PCT Pub. No.: WO2006/117692
PCT Pub. Date: Nov. 9, 2006

(65) Prior Publication Data
US 2009/0159654 A1    Jun. 25, 2009

(30) Foreign Application Priority Data

Apr. 28, 2005   (FR) ...................................... 05 04305

(51) Int. Cl.
*G06F 17/00* (2006.01)
(52) U.S. Cl. .......... 235/375; 65/117; 65/65; 219/121.85
(58) Field of Classification Search .................. 235/375; 219/121, 121.85; 65/117, 65
See application file for complete search history.

(56) References Cited

U.S. PATENT DOCUMENTS

| | | | | |
|---|---|---|---|---|
| 4,743,284 | A | * | 5/1988 | Mouly et al. ..................... 65/113 |
| 5,053,010 | A | * | 10/1991 | McGary et al. ................ 604/110 |
| 5,767,483 | A | * | 6/1998 | Cameron et al. ......... 219/121.85 |
| 6,638,440 | B1 | | 10/2003 | Grimard |
| 2001/0028390 | A1 | | 10/2001 | Hayashi |
| 2003/0029849 | A1 | * | 2/2003 | Trinks et al. ............. 219/121.69 |
| 2004/0035824 | A1 | | 2/2004 | Grimard |
| 2004/0186437 | A1 | | 9/2004 | Frenette et al. |
| 2005/0218126 | A1 | * | 10/2005 | Leyvraz ................... 219/121.69 |

FOREIGN PATENT DOCUMENTS

FR          2 690 862 A       11/1993
(Continued)

*Primary Examiner* — Michael G Lee
*Assistant Examiner* — Tabitha Chedekel
(74) *Attorney, Agent, or Firm* — Hoffman & Baron, LLP (57) ABSTRACT

Method of identifying a container (1) obtained by a process comprising the following steps: (A) starting from a blank (2) of the container (1), at least part of the said container (1) is formed; (B) a two-dimensional or three-dimensional marking zone (4), the temperature of which is maintained at a value below the glass transformation temperature of the constituent substrate, is provided in or on the substrate of the blank (2) and, in the said marking zone (4), an identification code (5) is reproduced by illumination (6) of the said marking zone (4) with at least one beam (7) of coherent monochromatic localized electromagnetic radiation to which the substrate is at least partially transparent, the said beam (7) being operated and controlled in order to remove or modify the constituent substrate of the wall (3) and to leave the identification code (5), in positive or negative form, in the said wall so that the said code is readable; and (C) at least the said marking zone (4) is annealed so as at least to reduce the differences in internal tension in the substrate between the said marking zone (4) and the rest of the said wall (3).

11 Claims, 3 Drawing Sheets

FOREIGN PATENT DOCUMENTS

| | | |
|---|---|---|
| GB | 2 324 985 A | 11/1998 |
| JP | 2002-182546 | 6/2002 |
| JP | 2005-035575 | 2/2005 |
| WO | WO 2004/084795 A1 | 10/2004 |

* cited by examiner

METHOD OF IDENTIFYING A CONTAINER AND/OR A FINISHED ARTICLE OBTAINED FROM THE SAID CONTAINER, IN PARTICULAR FOR MEDICAL USE

The present invention relates in general to techniques for identifying a container, or a finished article obtained from the said container, at the end of a process that includes in particular a step of filling the said container with a product of interest.

As will be explained later, the present invention relates in particular, but not exclusively, to the identification or marking of a wall intended to form a container for medical use. In the rest of the text, the expression "container for medical use" is understood to mean any container used for the administration and/or the injection of medical produces such as, for example, medicaments, and also any analytical, testing or diagnostic container. Thus, the container for medical use may be a slide, a bottle, a vial or a tube, and it may be used to obtain an injection device, for example a syringe or an injection pen cartridge. The slides, bottles, vials or tubes may then be coated on one or more of their walls with a product of interest, such as for example a reactant that is in the form of a surface coating. The bottles, vials, tubes, syringes or cartridges may also be filled with a product of interest, for example a medicament in divided or undivided solid, gel, powder or liquid form, in order to obtain an administration, for example injection, device, or a finished, ready-to-use, article for medical, testing, analytical or diagnostic use. In the rest of the text, the expression "container filled with a product of interest" is understood to mean any container at least partly filled with the product of interest, and also any container one of whose walls is provided, by coating, spraying or any other similar technique, with a coating of the product of interest, such as for example a medicament, a vaccine or a reactant.

Consequently, the present invention relates to the identification or marking of a container for medical use, which may for example be made of a hot-formable glass or plastic, it being possible, but not restrictively, for the container to be obtained by a process comprising the following steps:
A1) at least one end part of a blank intended to form the container is heated until it has softened, and the end part thus softened is formed in order to obtain a predetermined shape of this part;
B1) the substrate of the blank formed in step (A1) is annealed so as to obtain, after cooling and complementary operations, the container in its definitive form or in an intermediate form.

The present invention also relates to any method of identifying, especially authenticating, at least one batch, or a plurality, of containers and/or finished articles obtained from the said containers after a process that may include, by way of non-limiting example, the following steps:
a) a plurality of containers is taken;
b) a product of interest, for example a liquid, is taken;
c) the various containers of the batch are filled with a predetermined quantity or dose of the product of interest; and
d) the various containers of the batch are closed off after being filled, for example with a means for ensuring the integrity of their respective contents.

The method or methods of identification considered by the present invention are employed for various purposes:
protection against copying or imitating the containers and/or the finished products obtained from them;
authentication of the original containers and finished articles;
traceability of the containers and/or the finished articles obtained from them, per batch or series, and possibly per unit, that is to say individual container and/or individual finished article; and
identification of the finished articles, in the distribution chains and/or in use, in particular within a regulatory and/or security context regarding the origin of the said finished articles.

Various ways of identifying a container and/or a finished article obtained from it have already been proposed. For example, it is known to identify various articles by external marking, labelling, printing, etching or other techniques. These known ways have the drawback whereby the information supported by the marking may be modified, destroyed or damaged, removed or copied, falsified or altered, thereby making these methods of identification not very effective and not very useful, in particular for combating fraud and copies.

Documents U.S. Pat. No. 6,638,440 and WO 2004/084795 disclose methods of printing or etching a mark on the external surface of a container.

Document US 2004/0186437 discloses a container having a permanent code on an exposed surface.

Document US 2001/0028390 discloses a method of making marks in a transparent material.

Document GB 2 324 985 discloses a method of providing a body of glassy thermoplastic polymeric material with a mark invisible to the naked eye.

Document FR 2 690 862 discloses a method of engraving an inscription as the internal face of a container.

According to document FR-A-2 665 855, it has been proposed to identify containers, consisting of glass receptacles, by a marking obtained within the actual wall of the said container, individually defined by an elementary point or modification of the substrate, for example by means of laser illumination. Such a marking method has the drawback of weakening the substrate of the container, which, for some applications, for example in the health field, is unacceptable or prohibited.

The object of the present invention is to remedy the drawbacks emphasized above.

The present invention proposes a method of identification by providing a mark integrated or incorporated definitively in the substrate of the container without thereby significantly affecting the mechanical properties or characteristics, including for example, the impact strength, of the container thus marked.

The present invention proposes a method of identifying a container for medical or diagnostic use, intended to hold a product of interest, the said container being obtained by a process characterized in that it comprises at least the following steps during which:
(B) a two-dimensional or three-dimensional marking zone, the temperature of which is maintained at a first temperature, is provided in or on the substrate of a blank intended to constitute the said container and, in the said marking zone, an identification code is reproduced by illumination of the said marking zone with at least one beam of coherent monochromatic localized electromagnetic radiation to which the substrate is at least partially transparent, the said beam being operated and controlled in order to remove or modify the constituent substrate of the wall and to leave the identification code, in positive or negative form, in the said wall so that the said code is readable; and
(C) at least the said marking zone is annealed by heating it to a second temperature strictly above the said first temperature so as at least to reduce the differences in internal tension in the substrate between the said marking zone and the rest of the said wall.

According to one advantageous embodiment, the first temperature is chosen so as to be strictly below the glass transformation temperature of the constituent substrate of the said container.

According to a preferred embodiment, during a step (A) carried out before the step (B), the blank is obtained by at least one of the techniques chosen from the group comprising: cutting, deburring, hot forming, hot deformation of at least one end portion of the blank after this end portion has been heated up to a temperature that permits the said deformation.

This method makes it possible in particular to obtain an injection device, for example a syringe, for injecting a product of interest, for example a medicament in divided solid or liquid form, comprising a container intended to hold or contain (after being filled) the said product, the said container being made of a substrate, for example a glass substrate, in or on which a two-dimensional or three-dimensional marking zone is provided, an identification code being reproduced in the said marking zone so that it is readable.

A method according to the invention makes it possible to obtain an integrated and indelible mark that does not affect the mechanical properties of the container, including its impact strength, and does so without complicating the process for manufacturing the said container.

Preferably, the method defined above may be integrated into a more general method of identifying a batch of finished articles obtained together after a process as described above.

The invention also proposes a method of identifying, especially authenticating, at least one batch, or a plurality, of containers and/or finished articles obtained from the containers after a process which comprises at least the following step:

(AA) a plurality of containers, each having at least one wall, is taken, characterized in that at least the following additional steps are carried out:

(AB) at least one intrinsic identification code is generated or produced for the batch;

(AC) the said plurality of containers is marked by providing a two-dimensional or three-dimensional intrinsic marking zone in or on the wall of each container and reproducing, so as to be readable, the said intrinsic identification code in or on each container identified by the latter, by the removal or modification of the constituent substrate of the wall;

(AD) at least one extrinsic identification code, relating to the product of interest intended to fill, or filling, the containers of the batch, is generated or produced;

(AE) the said plurality of containers intended to be filled or filled with the product of interest is marked again, by associating with each container an extrinsic marking means that reproduces, so as to be readable, each extrinsic identification code; and (AF) whereby each finished article is at least partly identified by reading its intrinsic and/or extrinsic identification codes.

This method of identifying finished articles may be employed independently of the specific method of identifying a container, defined above, that is to say with any method of identifying a container other than that considered above.

Such a method has the major advantage of being able to ensure traceability of a finished article, after a container has been filled, individually, and traceability being from manufacturer right up to the point of use, practically without any possibility of falsification or fraud.

The term "identification code" is understood to mean any elementary sign or combination of elementary signs, signifying or supporting information, such as numerals, letters, symbols, barcodes, or other characters, or else a representation such as a trademark or logotype.

In particular, the information thus supported or signified may or may not be encrypted.

The term "identification code" is therefore also understood to mean information that is not necessarily itself encoded.

Such an identification code, for example when it is alphanumeric, may be generated randomly or may result from particular data processing, such as counting.

Once this identification code has been identified, by reading it with the naked eye or using specific reading or recognition means, it is intended to allow access to various items of information such as, for example, the day, the date and the time of manufacture of the container and/or of the filling operation, the identity of the manufacturer of the container and/or of that of whoever added the product of interest, details about the process for obtaining the container, and its contents, the nature of the product of interest, and any other necessary information.

The term "laser" is understood to mean any device capable of emitting high-energy beams including, in addition to conventional lasers, electron beams, ion beams, synchrotron radiation beams and equivalents, making it possible to focus a local energy density of high level, capable of inducing, in the substrate of the wall, permanent modifications that are readable or not to the naked eye or are readable with a suitable reading or recognition instrument. The term "readable" is understood to mean the feature whereby the identification code can be detected or recognized, by the naked eye or with a suitable reading or recognition instrument, in relation to the differentiated features of the substrate in the marking zone. The term "intrinsic identification" is understood to mean any feature or marking that cannot be removed and is specific to a container. The term "extrinsic identification" is understood more particularly to mean any feature specific to a container that has been attached or affixed subsequent to or at the same time as the filling of the container.

The present invention will now be described with reference to the appended drawings in which.

Not restrictively, the containers 1 in the examples illustrated are syringe bodies made of glass, these being intended to hold a product 10 of interest. The containers 1 may of course be cartridges, tubes, bottles, vials or slides, made of other materials, for example plastic. Likewise, the product 10 of interest may be a medicament, a vaccine, a contrast, test or analysis product, a reactant or any other equivalent product. The product 10 of interest may also be a physiological fluid, which may or may not be taken from a living being, or any other fluid to be sampled, analysed or stored.

Figure 1:
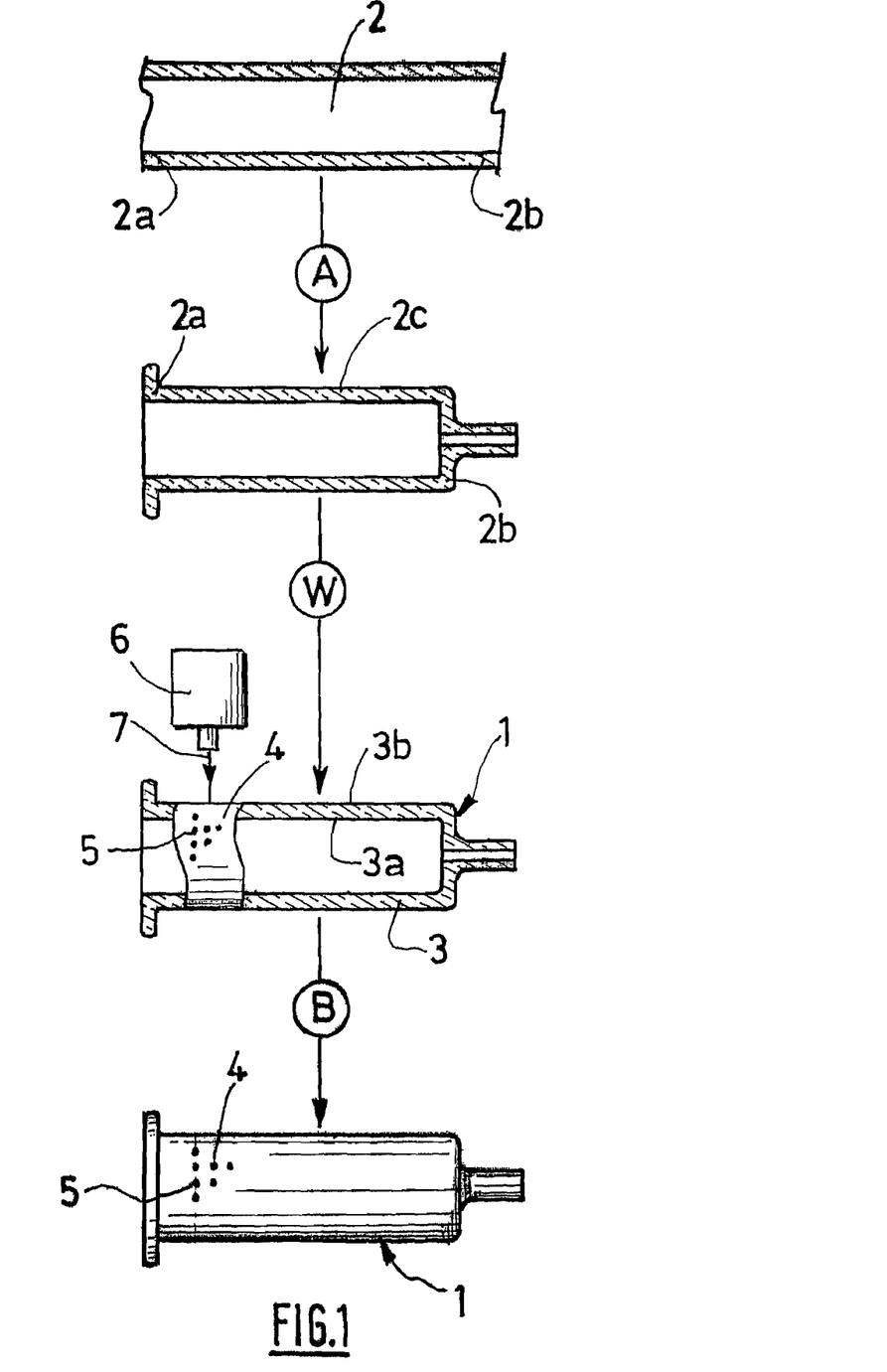
FIG. 1 shows schematically the steps of the method followed in order to obtain a container that includes an identification means according to the invention.

A method will now be described, with reference to FIG. 1, for obtaining a container 1 for medical use with an identification means according to the invention, this container 1 having a wall 3 made of a rigid thick substrate, which can be formed and/or deformed hot, for example a glass substrate.

This method comprises the following steps:

to begin with, a blank 2 is obtained from a glass tube, cut to the length or height of the container 1 to be obtained;

in step (A), two end parts 2a and 2b of this blank 2 are heated until the glass softens and the softened end parts 2a and 2b are deformed by means (not shown) in order to obtain features of predetermined shape, namely a flange at the end part 2a and a ferrule at the end part 2b respectively; during this step (A), the intermediate part 2c, located between the two end parts 2a and 2b, remains relatively cool, since it is not heated, and in any case remains at a temperature below the glass transformation temperature;

before step (B) defined below, the step (W) is carried out in which a two-dimensional or three-dimensional marking zone 4 is provided in or on the wall 3 of the blank 2, at any suitable point in the intermediate part 2c maintained at a first predetermined temperature, and an identification code 5 is reproduced in this marking zone 4 by illumination, for example from a laser source 6, of the marking zone 4 with a beam 7 of coherent monochromatic light to which the substrate (for example a glass substrate) is at least partially transparent, and to do so by operating and controlling the beam 7 in order to remove or modify the constituent substrate of the wall 3 and to leave an identification code 5, in positive or negative form, in the said wall so that the said code is readable. As an example, a succession of discrete illuminations is performed and the identification code consists of an arrangement of microbubbles or microspheres in the substrate having properties (for example light transmission properties) that differ from the rest of the substrate; and then in step (B), the substrate of the blank 2, formed in step (A) and identified in step (W), is annealed by heating the substrate to a second temperature strictly above the first temperature in order to anneal the said substrate, at least in the marking zone 4, and to obtain, after cooling, sufficient relaxation of the undesirable internal tensile stresses in the wall within the said marking zone 4. With an identification code formed for example by an arrangement of discrete elements, such as for example dots or dashes, the marking zone 4 may be divided into individual marking zones each comprising one or more discrete elements of the identification code. It will then be possible to perform separate annealing operations on each individual marking zone or on several of them, in succession or simultaneously.

Figure 7:
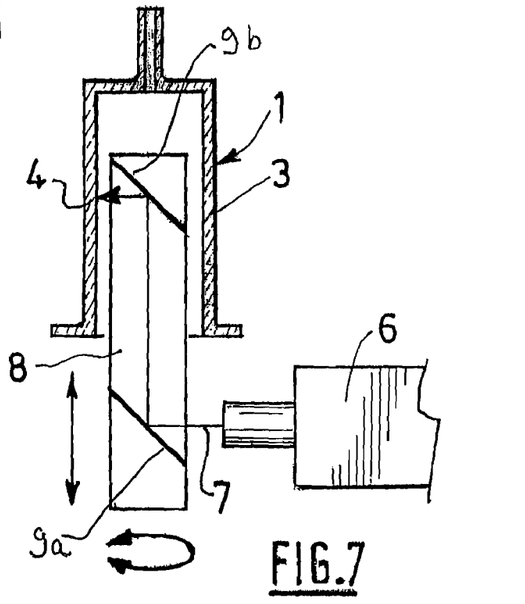
FIGS. 7 and 8 show schematically, and respectively, two ways of obtaining the identification means shown in FIG. 6.

At each of the elementary points of the identification code, the substrate is transformed (vaporized or modified) by focusing at least one laser beam 7 thereonto and by moving the focal point by suitable means, such as those represented for example in FIG. 7, by using a pulsed source 6 of suitable coherent monochromatic light. The power density of the laser 10 at the focal point is at least $10^6$ W/cm$^2$ and the pulse duration is for example of the order of a few femtoseconds, in such a way that the energy density of each pulse is sufficient to transform the substrate at the focal point of the beam. For example, it is possible to use an Nd:YAG laser operating at a wavelength of 1.06 μm with a substrate transparent at this wavelength. The means for moving the focal point of the beam relative to the blank 2 comprise, in general, movable mirrors 9a, 9b placed along the path of the beam 7, the movement of which may be controlled by a motor drive system that can be controlled by a computer program, and suitable control or operating means. In general, it is possible to move either the wall 3 or to modify the path of the beam 7, or to do both simultaneously. In the examples illustrated, only the path is modified.

The method described above may be carried out in various alternative ways:

the first temperature is chosen so that it is strictly below the glass transformation temperature of the constituent substrate of the container;

the blank 2, including the marking zone 4, is annealed in its entirety in a single step (B); or the marking zone 4 is annealed independently of step (B) in an additional step, for example by means of a heat source separate from that used to carry out step (B), for example a flame, a microflame or at least one defocused laser beam.

Preferably, the marking zone 4 is provided in the thickness of the wall 3 of the container 1, at some distance from its internal face 3a and/or from its external face 3b.

Figure 6:
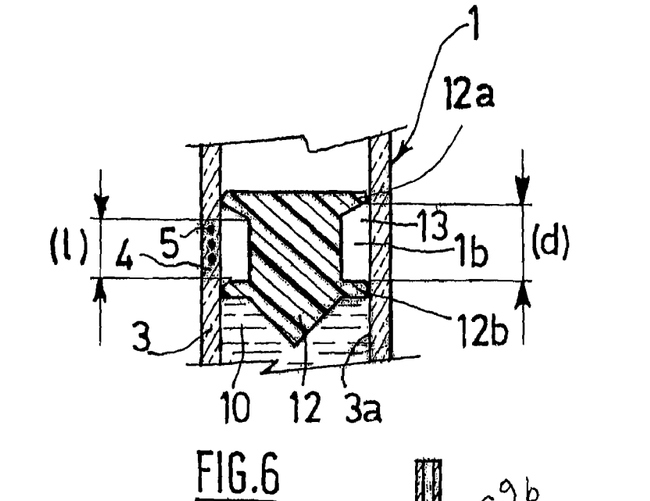
FIG. 6 illustrates a portion of an identified container in one embodiment of the present invention.

As a variant, the marking zone 4 is provided on the wall 3 of the container 1, for example on the internal face 3a in the useful part 1b of the container 1, intended subsequently to be filled with the product 10 of interest. In this latter case, with reference to FIG. 6, as described below, the product 10 of interest subsequently fills the container 1 and the latter is closed off by means 12 for ensuring integrity of the contents, for example a piston having at least two sealing lips 12a and 12b that seal against the wall 3 of the container 1. In this example, the lips 12a and 12b lie in two approximately parallel planes perpendicular to the axis of the container 1 and leaving a not necessarily sealed gap 13 between them. In this case, to avoid any loss of sealing generated by a marking zone 4 emerging on the internal face 3a of the container 3, the length (l), or height, of the marking zone (4) along the axis of the container 1 is less than the distance (d) separating the two lips 12a and 12b that define the gap 13. In this way, when the piston 12 is moved towards the ferrule, at no moment is the useful part 1b of the container 1 in communication with the outside via the leakage path provided by the surface marking zone 4.

Figure 8:
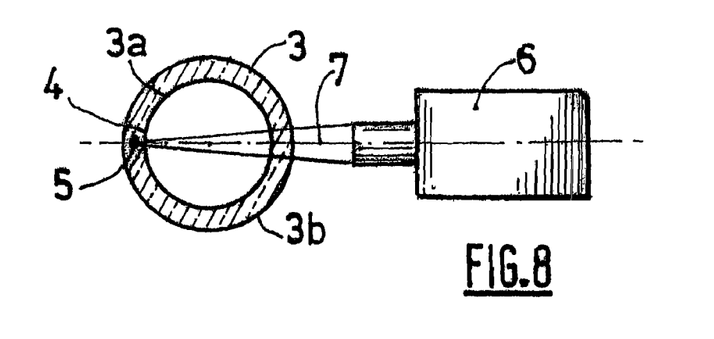

The marking zone 4 may also be provided on the internal face 3a of the wall 3, away from the useful part 1b of the container 1. Likewise, when the container 1 is a syringe provided with a flange, the marking zone 4 may be provided on the flange. When the marking zone 4 is provided on the internal face 3a of the wall 3 of the container 1, various means may be used to move the focal point of the pulsed laser beam 7. In FIG. 7, a device 8 comprising mirrors 9a, 9b is used, the said mirrors being able to be rotated and/or moved translationally inside the container 1 by mechanical means controlled by a motor drive system that may be controlled by a suitable computer program. In FIG. 8, the laser beam 7 passes through the wall 3 of the container 1 on the side facing the marking zone 4, before reaching the internal face 3a at its focal point.

Figure 5:
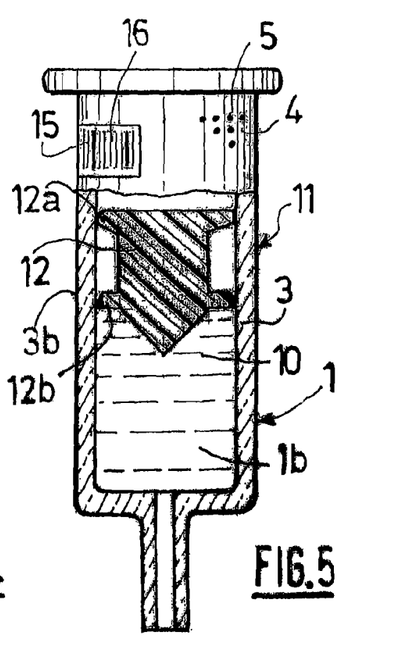

In total, as shown in FIG. 5, with regard to a medicament in divided or undivided solid, gel, powder or liquid form as product 10 of interest, the method described above makes it possible to obtain an injection device 11, for example a syringe, comprising a container 1 intended to hold or containing the said product 10 of interest, the wall 3 of which is made of a thick rigid substrate, for example a glass substrate, and in which wall a two-dimensional or three-dimensional marking zone 4 is provided, an identification code 5 being reproduced so as to be readable in the said marking zone 4. When the container 1 is filled, in order to provide a ready-to-use injection device 11, means 12 for ensuring the integrity of the contents close off the useful part 1b of the receptacle or container 1. With regard to a syringe-type injection device 11, these means 12 consist of at least one piston, made of an elastomeric material, comprising or forming two sealing lips 12a and 12b for sealing against the internal wall 3a of the container 3, the said lips lying in two approximately parallel respective planes, each perpendicular to the axis of the container 1, and leaving between them a not specifically sealed gap 13. In an alternative form (not shown), the injection device 11 may have several pistons placed one behind the other. Likewise, the lips 12a, 12b may define end sealing zones, which seal against the wall 3a, which are not parallel and/or not perpendicular to the axis of the container 1.

Of course, step (A) consisting in heating the end parts 2a and 2b of the container is carried out optionally. The identification method according to the present invention has the following alternative ways of implementing it, these being considered independently of one another, or in combination:

- during step (A), defined above, the said wall is formed by at least one of the techniques chosen from the group comprising: cutting, deburring, hot forming, hot deformation of at least one end portion of the said blank after this end part has been heated up to a temperature that permits the said deformation;
- the blank, including the marking zone, is annealed in its entirety during the said step (C);
- during the said step (C), the marking zone is annealed with a heat source different from that used for annealing the entire said blank, this heat source comprising, for example, at least one flame, at least one microflame or at least one defocused laser beam;
- the identification code consists of discrete elements and, during the said step (C), the said discrete elements are annealed individually or in groups by means of the said separate heat source;
- the marking zone is provided in the thickness of the wall of the container, at some distance from its internal face and/or from its external face;
- the marking zone is provided on the wall of the container;
- the marking zone is provided on the internal face of the wall of the container; and
- the wall is used to form, at least in part, a container for medical use chosen from the group comprising a syringe, a bottle or vial, a cartridge, a tube, a slide, intended to hold a product of interest, chosen from the group comprising a medicament, a vaccine, a product, a physiological fluid, in divided or undivided solid, gel, powder or liquid form.

The present invention therefore proposes a container for medical or diagnostic use, intended to hold a product of interest, in divided or undivided solid, gel, powder or liquid form, characterized in that at least one wall of the said container is provided with at least one two-dimensional or three-dimensional marking zone in which at least one identification code is reproduced so as to be readable.

The present invention also relates to an injection device for injecting a product of interest, for example a medicament in divided or undivided solid, gel, powder or liquid form, the said injection device comprising at least one container intended to hold or containing the said product of interest, the said container including at least one two-dimensional or three-dimensional marking zone in which at least one identification code is reproduced so as to be readable.

Such a device may have the following embodiments, these being considered independently of one another or in combination:

- the marking zone is provided in the thickness of the wall of the container, at some distance from its internal face and/or from its external face;
- the marking zone is provided on the external face of the wall of the container;
- the marking zone is provided on the internal face of the wall of the container, in the useful part of the latter, the said part being intended to hold or containing the product of interest;
- it contains the product of interest and is closed off by means for at least partly ensuring the integrity of the contents, the said means defining at least two end sealing zones, which seal against the wall of the container, and leaving a gap between them; the length (l), or height, of the marking zone, along the axis of the container is less than the distance (d) separating the two end sealing zones that define the said gap.

Figure 2:
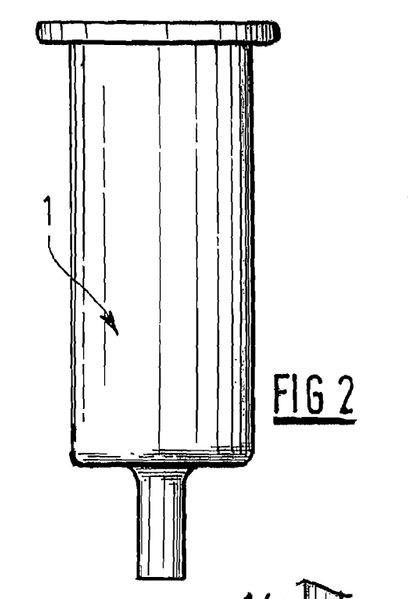
FIGS. 2 to 5 describe schematically the various steps of a method that results in finished articles identified according to the present invention.

The identification method described above may be integrated into or form part of a method of identifying, especially authenticating, at least one batch, or a plurality, of containers 1 and/or finished articles 11, consisting for example of ready-to-use injection devices, described above, which have been obtained together at the end of a process comprising at least the following steps:

(a) a plurality of containers 1 is provided, each having a wall 3 made of a rigid thick substrate, cf. FIG. 2;
(b) a product 10 of interest, for example a liquid product, is provided and dispensed by means of a dispensing means 14; cf. FIG. 4;
(c) the various containers 1 of the batch are filled with a predetermined quantity or dose of the product 10 of interest; cf. FIG. 4; and
(d) the various containers 1 of the batch, after their useful part 1b has been filled, are closed off for example with means 12 for ensuring the integrity of their respective contents (cf. FIG. 5).

Figure 3:
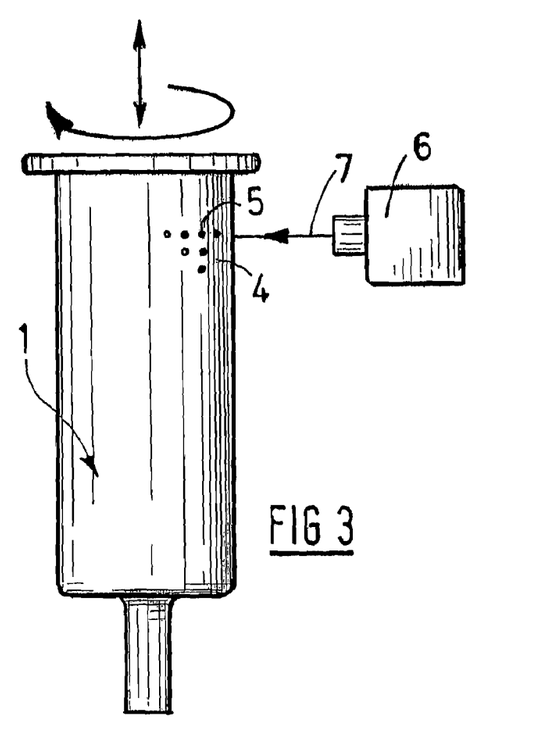
Figure 4:
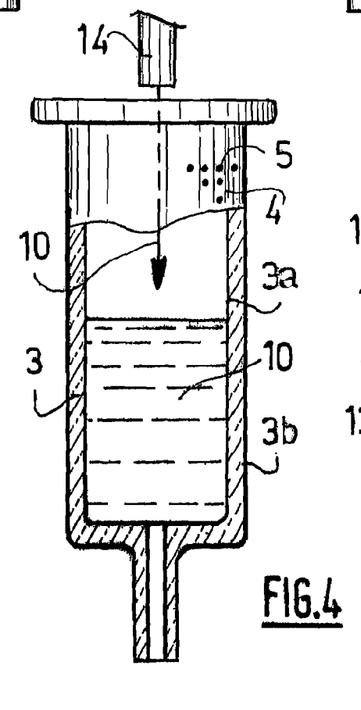

This identification method comprises the following steps, in combination:

(AB) a series of respectively different intrinsic identification codes 5 for the batch is generated or provided, the number of codes being the same as the number of containers 1, and assigned to the respective containers, so that a container 1 is identified by a single intrinsic identification code 5 that differs from that of another container 1;

(AC) according to FIG. 3, the plurality of containers 1, in the empty state, are marked by providing, in or on the wall 3 of each container 1, a two-dimensional or three-dimensional intrinsic marking zone 4 and by reproducing, in a readable manner, each intrinsic identification code 5 in or on the container 1 identified by the said code, and to do so by removing or modifying the constituent substrate of the wall 3 of the container 1; this step may be identical to that described above with reference to FIG. 1. The code may be reproduced by physical, chemical, optical or equivalent means;

(AD) after the filling step (C) shown in FIG. 4, a series of identical or alternatively different, extrinsic identification or information codes 16 is generated or provided, the said codes being respectively correlated with the intrinsic identification codes 5, the extrinsic identification codes 16 supporting at least some information in common with the intrinsic identification codes 5, relating to the product 10 of interest with which the containers 1 of the batch have been filled; the correlations thus established are stored in memory;

(AE) as shown by FIG. 5, the plurality of containers 1 filled with the product 10 of interest is again marked, by associating with each container 1 (filled 1b) an extrinsic marking means 15, which may or may not be different from the intrinsic marking zone 4 and reproducing, so as to be readable, each extrinsic identification code 16 on the outside of each container 1, now filled 1b; and (AF) whereby, each finished article 11 is identified by reading these intrinsic identification codes 5 and extrinsic identification codes 16, and by checking the correlation of the codes read with each of the correlations established and stored in memory in step (AD).

With reference to the above description, the intrinsic marking zone 4 may be provided in the thickness of the wall 3 of each container 1, or on the wall 3 of each said container 1. In the latter case for example, the intrinsic marking zone 4 is provided on the internal face 3a of the wall 3 of the container 1, in the useful part 1b of the latter, intended to be filled with the product 10 of interest and to be closed off by the means 12 for ensuring integrity of the contents of each container 1.

As an example, the extrinsic identification code 16 consists of a label attached to or affixed on the external face 3b of the wall 3 of the container 1.

As an example, the extrinsic marking means 15 may consist of a recessed surface, obtained by abrasion on the outside and on the wall 3 of each container 1, and the extrinsic identification code 16 is reproduced, in the recessed surface, for example by printing.

Of course, the method of identification defined above or described may be implemented by computer means according to a procedure exemplified below:

- a first operator, for example the manufacturer of the batch of empty containers 1, generates a first database ranked by intrinsic identification codes 5 and associated with the said batch;
- a second operator, for example the one filling the batch of containers 1, generates a second database, again ranked by intrinsic identification codes 5, in which second database the extrinsic identification codes 16 are stored, these being correlated with the respective intrinsic identification codes 5; and
- where appropriate, a third operator, for example the person using the finished articles 11, reads at least one of the intrinsic identification codes 5 and/or extrinsic identification codes 16 and accesses the second database in order to authenticate the container 1 and the product 10 of interest.

The method described above also has the following alternative ways of implementing it, these being considered independently of one another or in combination:

- in at least one of the said steps (AB) or (AD), an intrinsic identification code and/or an extrinsic identification code per container are/is generated or provided in such a way that a container and the product of interest that it is intended to contain or does contain are identified in a unique manner by the combination of at least one intrinsic identification code and an extrinsic identification code;
- the said intrinsic marking zone and the said extrinsic marking zone are separate and not superposed;
- the method includes a correlation step during which each intrinsic identification code is made to correspond to an extrinsic identification code, or vice versa, and the said correspondences are stored in memory;
- the intrinsic marking zone is provided in the thickness of the wall of each container;
- the intrinsic marking zone is provided on the wall of each container;
- the intrinsic marking zone is provided on the internal face of the wall of each container;
- the intrinsic marking zone is provided in the useful part of the container intended to be in contact with the product of interest, and to be closed off by means for ensuring the integrity of the content of each said container;
- the extrinsic marking means consists of a label attached to or affixed on the outside of each container;
- the extrinsic marking means consists of a recessed surface abraded on the outside on the wall of each container, and the intrinsic identification code is reproduced in the recessed surface, for example by printing;
- the container is for medical use and chosen from the group comprising a syringe, a bottle or vial, a cartridge, a tube or a slide, and in that the product of interest is chosen from the group comprising a medicament, a vaccine, a product or a physiological fluid, and is in divided or undivided solid, gel, powder or liquid form; and
- the container has several intrinsic identification codes and/or several extrinsic identification codes.

Preferably, to implement the method of identification according to the invention, a container 1 will be used which is made of a material such as glass or plastics and the walls of which are rigid and have a thickness of greater than 50 microns. These materials, combined with the method of identification according to the invention, will make it possible to guarantee the integrity and the correct preservation of the product 10 of interest, and also its traceability.

The invention claimed is:

1. Method of marking a container (1) for identification purpose for medical or diagnostic use, intended to hold a product (10) of interest, the said container (1) being obtained by a process characterized in that it comprises at least the following steps during which:

(B) a two-dimensional or three-dimensional marking zone (4), the temperature of which is maintained at a first temperature, is provided in or on the substrate of a blank (2) intended to constitute the said container (1) and, in the said marking zone (4), an identification code (5) is reproduced by illumination (6) of the said marking zone (4) with at least one beam (7) of coherent monochromatic localized electromagnetic radiation to which the substrate is at least partially transparent, the said beam (7) being operated and controlled in order to remove or modify the constituent substrate of the wall (3) and to leave the identification code (5), in positive or negative form, in the said wall so that the said code is readable; and (C) at least the said marking zone (4) is annealed, by a heat source separate from the said at least one beam (7), by heating it to a second temperature strictly above the said first temperature so as at least to reduce the differences in internal tension in the substrate between the said marking zone (4) and the rest of the said wall (3).

2. Method according to claim 1, characterized in that the said first temperature is chosen so as to be strictly below the glass transformation temperature of the constituent substrate of the said container (1).

3. Method according to claim 1, characterized in that, during a step (A) carried out before the said step (B), the said blank (2) is obtained by at least one of the techniques chosen from the group comprising: cutting, deburring, hot forming, hot deformation of at least one end portion (2a) of the said blank (2) after this end portion (2a) has been heated up to a temperature that permits the said deformation.

4. Method according to claim 1, characterized in that the blank (2), including the marking zone (4) is annealed in its entirety during the said step (C).

5. Method according to claim 4, characterized in that, during the said step (C), the said marking zone (4) is annealed with a heat source different from that used for annealing the entire said blank (2), this heat source comprising, for example, at least one flame, at least one microflame or at least one defocused laser beam.

6. Method according to claim 5, characterized in that the said identification code (5) consists of discrete elements and in that, during the said step (C), the said discrete elements are annealed individually or in groups by means of the said separate heat source.

7. Method according to claim 1, characterized in that the marking zone (4) is provided in the thickness of the wall (3) of the container (1), at some distance from its internal face (3*a*) and/or from its external face (3*b*).

8. Method according to claim 1, characterized in that the marking zone (4) is provided on the wall (3) of the container (1).

9. Method according to claim 1, characterized in that the marking zone (4) is provided on the internal face (3*a*) of the wall (3) of the container (1).

10. Method according to claim 1, characterized in that the said wall (3) is used to form, at least in part, a container (1) for medical use chosen from the group comprising a syringe, a bottle or vial, a cartridge, a tube, a slide, intended to hold a product (10) of interest, chosen from the group comprising a medicament, a vaccine, a product, a physiological fluid, in divided or undivided solid, gel, powder or liquid form.

11. Method according to claim 1, wherein said blank (2) is pre-formed prior to the beam (7) removing or modifying the constituent substrate of the wall (3) in leaving the identification code (5).

* * * * *